US005851792A

United States Patent [19]
Shen et al.

[11] Patent Number: 5,851,792
[45] Date of Patent: Dec. 22, 1998

[54] AGLUCONE ISOFLAVONE ENRICHED VEGETABLE PROTEIN WHEY WHEY PROTEIN MATERIAL AGLUCONE ISOFLAVONE MATERIAL HIGH GENISTEIN CONTENT MATERIAL AND HIGH DAIDZEIN CONTENT MATERIAL AND PROCESS FOR PRODUCING THE SAME FROM A VEGETABLE PROTEIN WHEY

[76] Inventors: Jerome Shen, 5937 Keith Pl., St. Louis, Mo. 63109; Mark A. Roussey, 5523-A Ed-Lou La., St. Louis, Mo. 63128; Barbara A. Bryan, 7039 Pershing Ave., St. Louis, Mo. 63130; Maryann C. Allred, 168 Bohnenstiehl Rd., Collinsville, Ill. 62234

[21] Appl. No.: 627,301

[22] Filed: Apr. 3, 1996

[51] Int. Cl.$^6$ .............................. C12P 21/06; C12P 19/62
[52] U.S. Cl. ........................ 435/68.1; 435/76; 435/125; 435/200; 435/272; 514/2; 514/455; 514/456; 536/8; 530/378; 530/412; 530/414; 530/420; 549/402; 549/403
[58] Field of Search ........................... 435/76, 68.1, 125, 435/200, 272; 514/2, 455, 456; 530/378, 41.2, 414, 420; 536/8; 549/402, 403

[56] References Cited

U.S. PATENT DOCUMENTS

| | | | |
|---|---|---|---|
| 3,391,001 | 7/1968 | Sair et al. | 99/17 |
| 3,461,205 | 8/1969 | Mansfeld et al. | 424/195 |
| 3,870,805 | 3/1975 | Hayes et al. | 426/148 |
| 3,949,085 | 4/1976 | Feuer et al. | 424/283 |
| 4,064,277 | 12/1977 | Yokotsuka et al. | 426/331 |
| 4,157,984 | 6/1979 | Zilliken | 252/407 |
| 4,163,746 | 8/1979 | Feuer et al. | 260/345.2 |
| 4,218,489 | 8/1980 | Zilliken | 426/545 |
| 4,232,122 | 11/1980 | Zilliken | 435/52 |
| 4,259,358 | 3/1981 | Duthie | 426/46 |
| 4,264,509 | 4/1981 | Zilliken | 260/345.2 |
| 4,366,082 | 12/1982 | Zilliken | 252/404 |
| 4,366,248 | 12/1982 | Zilliken | 435/125 |
| 4,390,559 | 6/1983 | Zilliken | 426/545 |
| 4,428,876 | 1/1984 | Iwamura et al. | 260/123.5 |
| 4,841,077 | 6/1989 | Ito et al. | 549/402 |
| 4,889,921 | 12/1989 | Diosady et al. | 530/377 |
| 4,960,908 | 10/1990 | Ito et al. | 549/403 |
| 5,141,746 | 8/1992 | Fleury et al. | 424/195.1 |
| 5,320,949 | 6/1994 | Shen et al. | 435/68.1 |
| 5,637,561 | 6/1997 | Shen et al. | 514/2 |
| 5,637,562 | 6/1997 | Shen et al. | 514/2 |

FOREIGN PATENT DOCUMENTS

| | | | |
|---|---|---|---|
| 258669 | 12/1989 | Japan | 311/40 |
| 1514765 | 10/1989 | U.S.S.R. | |
| WO9 510512 | 4/1995 | WIPO . | |
| WO9 510529 | 4/1995 | WIPO . | |
| WO9 510530 | 4/1995 | WIPO . | |

OTHER PUBLICATIONS

"Objectionable Flavor of Soy Milk Developed During the Soaking Of Soybeans And Its Contrtol", by Matsuura et al., *J. of Food Science*, vol. 54, No. 3, pp. 602–605.

"B–Galactosidase–Inhibiting New Isoflavanoids Produced by Actinomycetes", by Hazato et al., *The Journal Of Antibiotics*, vol. XXXII, No. 3, pp. 217–222 (1979).

"A Sepcific Inhibitor For Tyrosin Protein Kinase From Pseudomonas", by Ogawara et al., Ogawara et al., *The J. of antiobiotics*, vol. XXXIX, No. 4, pp. 606–608.

"Control of Serum Lipids With Soy Protein", by J. Erdman, *The New England Journal Of Medicine*, vol. 333, No. 5, pp. 313–314 (1995).

*The Flavanoids, Advances In Research Since 1980*, pp. 125–209 (ed. by J. Harborne 1988).

"Induction of Mammalian Topoisomerase II Dependent DNA cleavage By Nointer–calative flavanoids,m Genistein And orobol", by Yamashita et al., *Biochemical Pharmacology*, vol. 39, No. 4, pp. 737–744 (1990).

"Soybean Utilization", pp. 64–66 (1987).

"Soybeans: Chemistry and Technology", pp. 187–188 (1978).

"B–Glucosidase From Soybeans Hydrolyze Daidzin And Genistin", by Matsuura, et al., *Journal of Food Science*, vol. 58, No. 1, pp. 144–147 (1993).

"Proposed Draft Standard For Soy Protein Products", Report of the Fifth Session of the Codex Committee on Vegetable Proteins, Ottawa, Canada, Feb. 6–10, 1989.

"Isoflavone Composition of American And Japanese Soybeans In Iowa: Effects Of Variety, Corp Year, and Location", by Heui–Ju Wang and Patrica A. Murphy, *J. Agric. Food Chem.*, vol. 42, pp. 1666–1673 (1974): pp. 1674–1677 (1974).

"Genistein, a Specific Inhibitor Of Tyrosine–Specific Protein Kinases", by Akiyama et al., *The Jr. of Biological chemistry*, vol. 262, No. 12, pp. 5592–5595.

"Mechanisms Of Action In NIH–3T3 Cells Of Genistein, An Inhibitor Of EGF Receptor Tyrosine Kinase Activity", by Linassier et al., *Biochemical Pharmacology*, vol. 39, No. 1. pp. 187–193 (1990).

"The Role of Soy Products In reducing risk Of Cancer", by Messina and Barnes, *Journal of the National Cancer Institute*, vol. 83, No. 8, pp. 541–546 (1991).

(List continued on next page.)

*Primary Examiner*—Herbert J. Lilling

[57] ABSTRACT

An aglucone isoflavone enriched vegetable protein whey, whey protein material, high genistein material, high daidzein material, and aglucone isoflavone material are provided, as well as a process for producing the same from a vegetable protein whey. Isoflavone conjugates in a vegetable protein whey are converted to isoflavone glucosides by treating the whey at a temperature and a pH for a period of time sufficient to effect the conversion. The isoflavone glucosides are converted to aglucone isoflavones by enzymatic reaction to produce an aglucone isoflavone enriched vegetable protein whey. Aglucone isoflavone whey protein material is recovered from the aglucone isoflavone enriched vegetable protein whey. A high genistein content material, a high daidzein content material, and an aglucone isoflavone material are produced from an alcohol extract of the aglucone isoflavone whey protein material.

53 Claims, No Drawings

OTHER PUBLICATIONS

"Effect Of Genistein On Topoisomerase Activity And On the Growth Of [VAL 12] Ha–ras– Transformed NIH 3T3 Cells", by Okura et al., *Biochemical and Biophysical Research Communications*, vol. 157, No. 1, pp. 183–189 (1988).

"Proceedings Of The American Association For Cancer Research", vol. 34, Mar. 1993, abstracts 999 and 3310.

"Genistein And Biochanin A Inhibit The Growth Of Human Prostate Cancer Cells But Not the epidermal Growth Factor Receptor tyrosine Autophosphorylation", by Petrerson and Barnes: *The Prostate*,22:335–345 (1993).

"Soybeans Inhibit Mammary Tumors In Models Of Breast Cancer", by Barnes et al., *Mutagens and Carcinogens in the diet*, pp. 239–253 (1990).

"Genistein Inhibition Of The Growth Of Human Breast Cancer Cells: Independence From Estrogen Receptors And The Multi–Drug Resistance Gene", by Peterson and Barnes, Biochemical and Biophysical Rresearch Communications, vol. 179, No. 1, pp. 661–667.

AGLUCONE ISOFLAVONE ENRICHED VEGETABLE PROTEIN WHEY WHEY PROTEIN MATERIAL AGLUCONE ISOFLAVONE MATERIAL HIGH GENISTEIN CONTENT MATERIAL AND HIGH DAIDZEIN CONTENT MATERIAL AND PROCESS FOR PRODUCING THE SAME FROM A VEGETABLE PROTEIN WHEY

BACKGROUND OF THE INVENTION

The present invention relates to an aglucone isoflavone enriched vegetable protein whey, an aglucone isoflavone enriched whey protein material, an aglucone isoflavone material, a high genistein content material, and a high daidzein content material, and processes for making the same from a vegetable protein whey.

Isoflavones occur in a variety of leguminous plants, including vegetable protein materials such as soybeans. These compounds include daidzin, 6"-OAc daidzin, 6"-OMal daidzin, daidzein, genistin, 6"-OAc genistin, 6"-OMal genistin, genistein, glycitin, 6"-OAc glycitin, 6"-OMal glycitin, glycitein, biochanin A, formononetin, and coumestrol. Typically these compounds are associated with the inherent bitter flavor of soybeans.

In the production of commercial products, such as vegetable protein isolates and concentrates, the focus has been to remove these materials. For example, in a conventional process for the production of a soy protein isolate in which soy flakes are extracted with an aqueous alkaline medium, much of the isoflavones are solubilized in the extract along with soy protein. The protein is precipitated from the extract by acidification of the extract and is separated to form an isolate, leaving a whey which retains much of the solubilized isoflavones. Residual isoflavones left in the acid precipitated protein isolate are usually removed by exhaustive washing of the isolate. The whey and washes are typically discarded. The isoflavones in vegetable protein whey include isoflavone glucosides (glucones), isoflavone conjugates, and aglucone isoflavones. Isoflavone glucosides have a glucose molecule attached to the isoflavone moiety of the compound. Isoflavone conjugates have additional moieties attached to the glucose molecule, for example, 6"-OAc genistin contains an acetate group attached to the six position of the glucose molecule. Aglucone isoflavones consist of an isoflavone moiety without an attached glucose molecule.

Soy whey contains three "families" of isoflavone compounds having corresponding glucoside, conjugate, and aglucone members: the genistein family, the daidzein family, and the glycitein family. The genistein family includes the glucoside genistin; the conjugates 6"-OMal genistin (6"-malonate ester of genistin) and 6"-OAc genistin (6"-acetate ester of genistin); and the aglucone genistein. The daidzein family includes the glucoside daidzin; the conjugates 6"-OMal daidzin, and 6"-OAc daidzin; and the aglucone daidzein. The glycitein family includes the glucoside glycitin, the conjugate 6"-OMal glycitin, and the aglucone glycitein.

While all the isoflavones are of interest in medical evaluation, the aglucones are the specific isoflavones of most interest. Genistein and daidzein may significantly reduce cardiovascular risk factors. "Plant and Mammalian Estrogen Effects on Plasma Lipids of Female Monkeys", *Circulation*, vol. 90, p.1259 (October 1994). Genistein and daidzein are also thought to reduce the symptoms of conditions caused by reduced or altered levels of endogenous estrogen in women, such as menopause or premenstrual syndrome. Further, it has recently been recognized that the aglucone isoflavones contained in vegetable material such as soybeans may inhibit the growth of human cancer cells, such as breast cancer cells and prostate cancer cells, as described in the following articles: "Genistein Inhibition of the Growth of Human Breast Cancer Cells, Independence from Estrogen Receptors and the Multi-Drug Resistance Gene" by Peterson and Barnes, *Biochemical and Biophysical Research, Communications*, Vol. 179, No. 1, pp. 661–667, Aug. 30, 1991; "Genistein and Biochanin A Inhibit the Growth of Human Prostate Cancer Cells but not Epidermal Growth Factor Receptor Tyrosine Autophosphorylation" by Peterson and Barnes, *The Prostate*, Vol. 22, pp. 335–345 (1993); and "Soybeans Inhibit Mammary Tumors in Models of Breast Cancer" by Barnes et al., *Mutagens and Carcinogens in the Diet*, pp. 239–253 (1990).

As noted above, the aglucone isoflavones include daidzein, genistein, and glycitein. These aglucones have the following general formula:

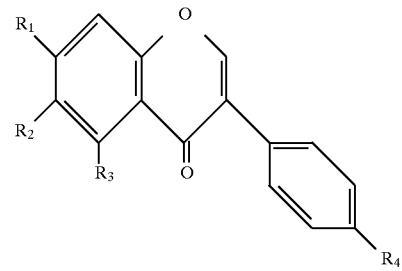

wherein $R_1$, $R_2$, $R_3$, and $R_4$ may be selected from the group consisting of H, OH and $OCH_3$ Genistein has the formula above where $R_1$=OH, $R_2$=H, $R_3$=OH, and $R_4$=OH, daidzein has the formula above where $R_1$=OH, $R_2$=H, $R_3$=H, and $R_4$=OH, and glycitein has the formula above where $R_1$=OH, $R_2$=$OCH_3$, $R_3$=H, and $R_4$=OH.

It is therefore to the aglucones and enrichment of a vegetable protein whey and a whey protein material with these compounds, and particularly to a high genistein content material, a high daidzein content material, and an aglucone isoflavone material to which the present invention is directed. The present invention is also directed to methods of making an aglucone enriched vegetable protein whey, an aglucone enriched vegetable whey protein material, a high genistein content material, a high daidzein content material, and an aglucone isoflavone material.

A general process for converting vegetable protein isoflavone conjugates to aglucone isoflavones is known, and is provided in the currently pending application U.S. Ser. No. 08/477,102 filed Jun. 7, 1995, owned by the assignee of the present application. Processes for converting isoflavone glucosides to aglucone isoflavones are also known. A process for converting isoflavone glucosides to aglucone isoflavones in a vegetable protein whey is provided in the currently pending application PCT/U.S./94/10699, owned by the assignee of the present application.

Other processes are also known in the art for converting isoflavone glucosides to aglucone isoflavones, such as described in Japanese Patent Application 258,669 to Obata et al. Such processes do not provide for the conversion of isoflavone conjugates to aglucone isoflavones or provide a high genistein content material, a high daidzein content material, or an aglucone isoflavone material. Furthermore, these processes achieve only a moderate extent of conversion of the glucosides to aglucones, and require a substantial period of time to effect this moderate extent of conversion. Therefore, such processes are not desirable for large scale commercial operations.

It is therefore an object of the present invention to provide an aglucone isoflavone enriched vegetable protein whey, and a process for producing the same from a vegetable protein whey.

It is a further object of the present invention to provide an aglucone isoflavone whey protein material, and a process for making the same from a vegetable protein whey.

It is a still further object of the present invention to provide a high genistein content material and a process for making the same from a vegetable protein whey.

It is yet a further object of the present invention to provide a high daidzein content material and a process for making the same from a vegetable protein whey.

It is a still further object of the present invention to provide an aglucone isoflavone material, and a process for making the same from a vegetable protein whey.

These and other objects are specifically achieved as described in the detailed description of the invention as set forth below.

SUMMARY OF THE INVENTION

This invention is an aglucone isoflavone enriched vegetable protein whey, and a process for producing an aglucone isoflavone enriched vegetable protein whey from a vegetable protein whey containing isoflavone conjugates. The process comprises treating a vegetable protein whey containing isoflavone conjugates at a temperature and a pH for a time period sufficient to convert the isoflavone conjugates to isoflavone glucosides. An enzyme is contacted with the isoflavone glucosides in the vegetable protein whey at a temperature and a pH for a time period sufficient to convert at least a majority of the isoflavone glucosides to aglucone isoflavones.

In one embodiment of the invention, the isoflavone conjugates are converted to isoflavone glucosides by treating the vegetable protein whey at a temperature between about 2° C. and about 121° C. and at a pH value of about 6 to about 13.7.

In another embodiment of the invention, the isoflavone glucosides are converted to aglucone isoflavones by contacting the isoflavone glucosides with an enzyme in the vegetable protein whey at a temperature between about 5° C. and about 75° C. and a pH value between about 3 and about 9.

High conversion rates of isoflavone conjugates to isoflavone glucosides, and isoflavone glucosides to aglucone isoflavones are realized. In one embodiment, at least 80% of the isoflavone conjugates are converted to isoflavone glucosides, and at least 80% of the isoflavone glucosides are converted to aglucone isoflavones.

In another aspect, this invention is an aglucone isoflavone whey protein material and a process for producing an aglucone isoflavone whey protein material from a vegetable protein whey containing isoflavone conjugates. An aglucone isoflavone whey protein material containing protein and aglucone isoflavones is recovered from an aglucone enriched vegetable protein whey. In one embodiment of the invention, the aglucone isoflavone whey protein material is recovered by at least one of ultrafiltration, heat coagulation, and dewatering.

In yet another aspect, this invention is a high genistein content material and a process for producing a high genistein content material from a vegetable protein whey containing isoflavone conjugates. An aglucone isoflavone whey protein material derived from a vegetable protein whey is extracted with an aqueous alcohol extractant to produce an aglucone isoflavone enriched extract. The extract is contacted with an adsorbent material for a time sufficient to separate a high genistein content material from the extract.

In another aspect, this invention is a high daidzein content material and a process for producing a high daidzein content material from a vegetable protein whey containing isoflavone conjugates. An aglucone isoflavone whey protein material derived from a vegetable protein whey is extracted with an aqueous alcohol extractant to produce an aglucone isoflavone enriched extract. The extract is contacted with an adsorbent material for a time sufficient to separate a high daidzein content material from the extract.

In still another aspect, this invention is an aglucone isoflavone material, and a process for producing an aglucone isoflavone material from a vegetable protein whey comprising isoflavone conjugates. An aglucone isoflavone whey protein material derived from a vegetable protein whey is extracted with an aqueous alcohol extractant to produce an aglucone isoflavone enriched extract. The extract is concentrated to between about 15% and about 30% of its original volume, and an aglucone isoflavone material is precipitated from the extract by adding water to the extract.

In one embodiment, a high genistein content material is separated from the aglucone isoflavone material. The aglucone isoflavone material is solvated in an aqueous alcohol solution, and the aqueous alcohol solution is contacted with an adsorbent material for a time sufficient to separate a high genistein content material.

In another embodiment, a high daidzein content material is separated from the aglucone isoflavone material. The aglucone isoflavone material is solvated in an aqueous alcohol solution, and the aqueous alcohol solution is contacted with an adsorbent material for a time sufficient to separate a high daidzein content material.

DESCRIPTION OF THE PREFERRED EMBODIMENTS

The starting material of the process is a vegetable protein whey, where a vegetable protein whey is defined as an aqueous solution of soluble proteins, isoflavones, and other water soluble compounds remaining after removal of vegetable protein curd from a vegetable protein extract. In a preferred embodiment the starting material is a soybean whey since the process is particularly suited for the production of aglucone isoflavone enriched whey, aglucone isoflavone whey protein material, high genistein content material, high daidzein content material, and aglucone isoflavone material from soybean materials.

The vegetable protein whey starting material contains isoflavone conjugates, isoflavone glucosides and aglucone isoflavones. For example, soy whey contains: isoflavone glucosides—genistin, daidzin, and glycitin; isoflavone conjugates—6--malonate esters of genistin, daidzin, and glycitin and 6"-acetate esters of genistin and daidzin; and aglucone isoflavones—genistein, daidzein, and glycitein. The isoflavones in a soy whey starting material are predominently isoflavone conjugates.

The vegetable protein whey starting material typically can be obtained as a byproduct of a conventional vegetable protein isolate production process. A vegetable protein source, such as soybean flakes from which oil has been removed by solvent extraction, can be extracted with an aqueous extractant having a pH above the isoelectric point of the protein in the vegetable protein source to produce an extract containing protein, isoflavones, and other compounds solubilized from the vegetable protein source by the extract. The extract is separated from vegetable material not soluble in the extract. The pH of the resulting extract containing the solubilized proteins and isoflavones is then adjusted to about the isoelectric point of the protein, about pH 4.4–4.6 for soy protein, in order to precipitate the protein from the extract. The precipitated protein is separated to produce a vegetable protein isolate, leaving the vegetable protein whey starting material. The isoflavones for the most part remain solubilized in the whey. To maximize isoflavone recovery in the whey, additional washing of the precipitated protein may be desirable, with each wash being added to the whey.

The vegetable protein whey starting material may be spray dried vegetable protein whey slurried in water. For ease of handling, the vegetable protein whey may be spray dried to recover whey protein (protein still soluble in the whey after precipitating protein isolate), isoflavones, and other compounds as a solid material. The spray dried material may be added to water to reconstitute a vegetable protein whey starting material. In a preferred embodiment, a slurry contains about 2–10 g of spray dried material for every 100 g of water to ensure that the whey is not too viscous, while providing sufficient isoflavones to produce the desired aglucone isoflavone enriched whey, aglucone isoflavone whey protein material, high genistein content material, high daidzein content material and aglucone isoflavone material.

In a first conversion step or operation, isoflavone conjugates in the vegetable protein whey starting material are converted to isoflavone glucosides to produce an isoflavone glucoside enriched vegetable protein whey. The conversion has been found to be dependant on the pH and the temperature of the whey.

The pH range for conversion of the isoflavone conjugates to isoflavone glucosides is from about 6 to about 13.5. The pH of the vegetable protein whey should be adjusted to the desired pH, if necessary. Soy protein whey typically has a pH value of about 4.4–4.6, and should be adjusted with a base or basic reagent to the desired pH range. The pH may be adjusted with any suitable base, caustic reagent, or basic reagent that will increase the pH of the system, including sodium hydroxide, potassium hydroxide, and calcium hydroxide. The conversion has been found to proceed more readily under relatively strong basic conditions, preferably pH 9–11. The pH should be maintained below pH 12 since isoflavone glucosides-genistin, daidzin, and glycitin, particularly daidzin—tend to be degraded at pH values of 12 and above. The reaction proceeds less readily at lower pH conditions, for example about pH 6, however, the reaction will proceed at higher temperatures and/or under increased pressure.

The temperature range for conversion of the isoflavone conjugates to isoflavone glucosides is from about 2° C. to about 121° C. The temperature range at which the conversion readily occurs depends on the pH of the whey. The inventors have found that the conversion occurs easily at lower temperatures when the pH is relatively high. For example, at a whey pH of about 11 the conversion occurs rapidly and efficiently at a temperature range of about 5° C. to about 50° C. At a whey pH of about 9 conversion occurs efficiently at a temperature range of about 45° C. to about 73° C. When the whey pH is relatively low the conversion occurs at higher temperatures. For example, at a whey pH of 6 the conversion occurs at a temperature range of about 80° C. to about 121° C. In a preferred embodiment the conversion is effected at about 35° C. at a whey pH of about 11. In another preferred embodiment, the conversion is effected at about 73° C. at a whey pH of about 9.

The time period required for substantially complete conversion of the isoflavone conjugates to isoflavone glucosides to occur is dependant on the pH and the temperature of the vegetable protein whey. Time periods range from 15 minutes up to 24 hours. Conversion occurs more rapidly at a higher pH and at a higher temperature. At a pH of about 9–10, conversion is substantially complete in about 4 to about 6 hours at 73° C. At a pH of about 10–11, conversion is substantially complete in about 30 minutes to about 1 hour at 35° C. In a most preferred embodiment the isoflavone conjugates are converted to isoflavone glucosides in about 45 minutes at a pH value of about 11 and at a temperature of about 35° C.

The first conversion step is remarkably efficient, converting from about 80% to about 100% of the isoflavone conjugates to isoflavone glucosides. Typically, conversion rates of at least 95% are observed. These high conversion rates are especially attractive for use in large scale commercial operations.

In a second conversion step or operation, the isoflavone glucosides produced in the first step, as well as isoflavone glucosides previously resident in the whey, are converted to aglucone isoflavones by an enzyme reaction. The conversion produces an aglucone isoflavone enriched vegetable protein whey from the isoflavone glucoside enriched whey.

The second conversion step has been found to be dependant on the concentration of enzymes present in the whey, and their characteristics. The enzymes required to effect the conversion are enzymes capable of cleaving the glucosidic linkage between the isoflavone moiety and the glucose molecule of the isoflavone glucosides. In a preferred embodiment the enzymes are saccharidase enzymes capable of cleaving 1,4-glucoside bonds. The concentration of enzymes required to convert the isoflavone glucosides to aglucone isoflavones is dependant on a variety of factors including the types of enzymes present in the whey, distribution of enzyme concentrations, activities of the enzymes, concentration of the isoflavone glucosides, and the pH and temperature of the whey during the conversion.

The enzymes may be naturally present in the vegetable protein whey, present from microbial growth in the whey, or may be added as a supplement to the whey. Enzyme that is naturally present, or is present from a microbial growth in the whey is referred to herein as "residual" enzyme, and enzyme that is added to the whey is referred to herein as "supplemental" enzyme.

Sufficient enzyme should be present in the whey to convert at least a majority, and preferably substantially all, of the isoflavone glucosides to aglucone isoflavones. Generally, if the residual enzymes in the whey are insufficient to effect the conversion, supplemental enzymes should be added to the whey. As noted above, a variety of factors determine whether the enzymes are present in adequate concentration to perform the conversion.

If supplemental enzyme is added, the supplemental enzyme should be added so that the total concentration of enzyme present is about 0.1% to about 10% by weight of the whey solids on a dry basis. In a preferred embodiment, supplemental enzyme is added to the whey regardless whether sufficient residual enzyme is present in the whey since addition of supplemental enzyme dramatically decreases the time necessary to effect substantially complete conversion of the glucosides to aglucones.

Supplemental enzymes are selected based on optimum activity at selected pH and temperature conditions, and cost effectiveness. The supplemental enzymes are enzymes capable of cleaving the bond between the isoflavone moiety and the glucose moiety of the isoflavone glucosides, such as saccharidase enzymes capable of cleaving 1,4-glucoside bonds. Preferred supplemental enzymes are commercially available alpha- and beta-glucosidase enzymes, beta-galactosidase enzymes, gluco-amylase enzymes, and pectinase enzymes. Particularly preferred are enzymes such as Biopectinase 100L (which is preferably utilized at a pH range of from about 3 to about 6), Biopectinase 300L (optimum pH range from about 3 to about 6), Biopectinase OK 70L (optimum pH range from about 3 to about 6), Biolactase 30,000 (optimum pH range from about 3 to about 6), and Neutral Lactase (optimum pH range from about 6 to about 8), all of which are available from Quest International, 1833 57th Street, Post Office Box 3917, Sarasota, Fla. 34243. Also particularly preferred are Lactase F (optimum pH range from about 4 to about 6), and Lactase 50,000 (optimum pH range from about 4 to about 6) which are available from Amano International Enzyme Co., Inc., Post Office Box 1000, Troy, Va. 22974. Other particularly preferred supplemental enzymes include: G-Zyme G990 (optimum pH from about 4 to about 6) and Enzeco Fungal Lactase Concentrate (optimum pH range from about 4 to about 6) available from Enzyme Development Corporation, 2 Penn Plaza, Suite 2439, New York, N.Y. 10121; Lactozyme 3000L (optimum pH range from about 6 to about 8) and Alpha-Gal 600L (optimum pH from about 4 to about 6.5) available from Novo Nordisk Bioindustrials, Inc., 33 Turner Road, Danbury, Conn. 06813; Neutral Lactase (optmum pH range from about 6 to about 8) available from Pfizer Food Science Group, 205 East 42nd Street, New York, N.Y. 10017; and Maxilact L2000 (optimum pH range from about 4 to about 6) available from Gist Brocades Food Ingredients, Inc., King of Prussia, Pa. 19406.

Once sufficient concentrations of enzymes are present, either from residual enzymes, supplemental enzymes, or both, the enzymes are contacted with the isoflavone glucosides in the whey at a pH and temperature and for a time period sufficient to convert at least a majority, and preferably substantially all, the isoflavone glucosides to aglucone isoflavones. If necessary, the pH of the isoflavone glucoside enriched whey should be adjusted to be within a pH range in which the enzymes actively react with the isoflavone glucosides. The pH range over which the combined residual enzymes and supplemental enzymes react with the isoflavone glucosides is from about 3 to about 9.

The inventors have found that the residual enzyme in the whey is active within a pH range of about 7 to about 9, although it is believed that the pH of the whey is lowered during the course of the reaction. The supplemental enzymes are active within an optimum pH range specified by the manufacturer of the enzyme, as shown above for several specific enzymes. Typically the supplemental enzymes are active either in a neutral pH range from about 6 to about 8, or in an acidic pH range from about 4 to about 6. The acidic enzymes have also been shown to be active at a pH of about 3.

The pH of the whey may be adjusted, in most cases reduced from the relatively high or basic pH of the first step, by the addition of one or more suitable acids such as acetic acid, sulfuric acid, phosphoric acid, hydrochloric acid, or any other suitable reagent. Preferably the reagent used will be a foodgrade acidic reagent or acid.

The temperature range for conversion of the isoflavone glucosides to aglucone isoflavones is from about 5° C. to about 75° C. The temperature significantly affects the activity of the enzymes, and therefore, the rate of the conversion. The supplemental enzymes may be active above 72.5° C., for example Alpha-Gal 600L is active at 75° C., however, it is preferred to conduct the conversion at lower temperatures to avoid enzyme deactivation. In a preferred embodiment, the conversion is effected between about 35° C. and about 45° C.

Preferably the enzyme reaction is conducted at the same temperature as the first conversion step, thereby eliminating the necessity of changing the whey temperature after the first conversion step. Most preferably, the second conversion step and the first conversion step are both conducted at 35° C.

It is also preferred that a constant temperature be maintained thoughout the conversion of the isoflavone glucosides to aglucone isoflavones. However, in some instances it may be desirable to raise, lower, or otherwise vary the temperature during the course of the reaction.

The time period required for the second conversion step depends on enzyme related factors, particularly concentration, and the temperature and pH of the whey. In most instances it is possible to achieve complete conversion within 24 hours, however, it is preferred that supplemental enzyme be added to dramatically increase the rate of the reaction. The selected supplemental enzyme, enzyme concentration, pH and temperature preferably cause substantially complete conversion within 2 hours, and most preferably within 1 hour.

The extent of conversion of isoflavone glucosides to aglucone isoflavones in the second conversion step is remarkable, typically from at least about 80% up to 100%. Conversion of at least 95% of the isoflavone glucosides to aglucone isoflavones is commonly acheived.

Following conversion of the isoflavone glucosides to aglucone isoflavones, the aglucone isoflavone enriched whey may be employed as desired without drying or removing protein in the whey, or alternatively, an aglucone isoflavone whey protein material can be recovered to concentrate the aglucone isoflavones in the protein material. Aglucone isoflavone whey protein material, as used herein, is defined as a material containing protein, aglucone isoflavones, and residual vegetable compounds that may be precipitated and separated from a vegetable protein whey. Protein material enriched with aglucone isoflavones can be recovered by conventional procedures such as ultrafiltration, heat coagulation, and dewatering. The resulting aglucone isoflavone whey protein material can be dewatered and dried by conventional means.

The aglucone isoflavone whey protein material can also be recovered from the whey by chilling the whey. The aglucone isoflavone whey protein material is insoluble in the chilled whey and may be separated as a precipitate from the whey by centrifuging the chilled whey. Preferably the whey is chilled to about 4° C. to precipitate the protein material.

In a preferred embodiment, the whey is concentrated in order to enhance recovery of the aglucone isoflavone whey protein material. It has been found that increasing the solids to liquid ratio in the whey by concentration of the whey increases the capture of the aglucone isoflavone whey protein material from the whey. The whey may be concentrated by heating, placing the whey under reduced pressure, or both. Preferably, the whey is concentrated to a solids to liquid ratio of about 1:3 to about 1:6, most preferably about 1:3.

A high genistein content material and a high daidzein content material may be produced from the recovered aglucone isoflavone whey protein material. As used herein, a high genistein content material is defined as a vegetable material containing at least 40% genistein, and most preferably at least 90% genistein, along with residual vegetable material, which is residual soy material if the high genistein content material is recovered from a soy whey. A high daidzein content material contains at least 40% daidzein along with residual vegetable material.

To produce the high genistein and high daidzein content materials, the aglucone isoflavone whey protein material is initially washed to remove undesired salts and sugars, and then dried. To wash the aglucone isoflavone whey protein material, the material is diluted with water, preferably to between about 1% solids to about 6% solids, and most preferably to about 2% solids. The wash water may be any temperature, however, it is preferred that the wash be between about 25° C. and about 75° C., and most preferably about 60° C. After washing the aglucone isoflavone whey protein material, the material is separated from the wash and dried. In a preferred embodiment, the material is separated by centrifuging the material, and decanting the supernatant from the material.

The aglucone isoflavone whey protein material may then be extracted with an aqueous alcohol extractant to remove the aglucone isoflavones from the whey protein and produce an aglucone isoflavone enriched extract. Low molecular weight alcohols such as methanol, and particularly ethanol, are preferred as the alcohol component of the extractant. The aglucone isoflavones have been found to be soluble at almost all alcohol concentrations of the extractant. The aglucone isoflavones are particularly soluble when the extractant contains between about 30% alcohol and about 90% alcohol, most preferably between about 60% alcohol and about 80% alcohol. Although aqueous alcohol is the preferred solvent, other solvents including water, acetonitrile, methylene chloride, acetone, and ethyl acetate and mixtures of these solvents may be used to effect the extraction of the aglucone isoflavones from the whey protein material.

The extraction is carried out using a minimal amount of extractant. It is preferred that the weight ratio of extractant to aglucone isoflavone whey protein material not exceed 11:1. In one embodiment, the material may be extracted using a countercurrent extraction process where the weight ratio of extractant to material is between about 6:1 to about 8:1. In another embodiment, the material may be extracted with two portions of the extractant, where the combined weight ratio of extractant to material does not exceed 11:1.

Although the extraction can be carried out at any pH, it is preferred that the extractant have a pH about the isoelectric point of the protein in the aglucone isoflavone whey protein material to minimize solubility of the protein in the extractant. Preferably the extractant has a pH value between about 3 and about 6, and most preferably about 4.5 when the whey protein is a soy whey protein.

The extraction may be conducted at any temperature up to the boiling point of the extractant, and preferably is conducted between about 25° C. and about 70° C. To reduce the time to extract the aglucone isoflavones from the aglucone isoflavone whey protein material it is preferred to conduct the extraction at a temperature elevated above room temperature, most preferably at about 60° C.

Following the extraction, a high genistein content material and a high daidzein content material may be separated from the aglucone isoflavone enriched extract by contacting the extract with an adsorbent material for a time sufficient to separate the high genistein and high daidzein content materials from the extract. In a preferred embodiment, the high genistein and high daidzein content materials are separated from the extract by reverse phase High Performance Liquid Chromatography ("HPLC"). Genistein and daidzein are separated from other isoflavones and impurities in the extract by eluting the extract through particles of an adsorbent material which releasably binds the genistein, daidzein, other isoflavones, and impurities in a compound specific manner, thereby enabling each of the compounds to be separated.

The aglucone isoflavone enriched extract is initially filtered to remove insoluble material that could plug an HPLC column. An HPLC column is prepared by packing a conventional commerically available HPLC column with a particulate adsorbent material which will releasably bind the genistein, daidzein, other isoflavones, and impurities in a compound specific manner. The adsorbent material may be any reverse phase HPLC packing material, however, a preferred packing material may be chosen by the criteria of load capacity, separation effectiveness, and cost. One such preferred packing material is Kromasil C18 16 $\mu$m 100 Å beads available from Eka Nobel, Nobel Industries, Sweden.

The filtered extract is passed through the packed HPLC column until all the binding sites of the column are fully saturated with isoflavones, which is detected by the appearance of isoflavones in the effluent from the column. The HPLC column may then be eluted with a polar eluent to effect the separation. In a preferred embodiment, the eluent is an aqueous alcohol. The aqueous alcohol eluent may have an alcohol content of between about 30% to about 90% alcohol, and preferably has an alcohol content of about 50% alcohol to provide both good separation and good solubility of the isoflavones. The alcohol is preferably methanol or ethanol, where ethanol is preferred when the high genistein or high daidzein content product materials are to be used in food or drug applications.

The high genistein and high daidzein content materials are collected from the column effluent. A fraction of effluent containing daidzein elutes from the column first, followed by a glycitein fraction, which is followed by the more polar genistein fraction. The daidzein and genistein fractions are collected as they elute from the column. The glycitein fraction may also be collected, if desired.

The alcohol in the fractions may be removed by evaporation, after which the high genistein and high daidzein content materials, and a high glycitein content material, can be recovered by conventional separation methods such as centrifugation or filtration. The recovered high genistein content material contains at least 40% genistein, and preferably at least 90% genistein, along with residual vegetable material, which is residual soy material if the genistein is recovered from a soy whey. The recovered high daidzein content material contains at least 40% daidzein, along with residual vegetable material, which typically includes a significant amount of glycitein.

In another embodiment of the invention, an aglucone isoflavone material is produced from the aglucone isoflavone enriched extract. As used herein, an aglucone isoflavone material is defined as a material containing at least 10% genistein and at least 5% daidzein, as well as other isoflavones and residual vegetable compounds.

Following extraction of the aglucone isoflavone whey protein material, the aglucone isoflavone enriched extract may be concentrated to facilitate precipitation of the aglucone isoflavones from the extract. The extract may be concentrated by heating the extract, placing the extract under reduced pressure, or both. In a preferred embodiment, the extract is concentrated to between about 15% and about 30% of its original volume.

An aglucone isoflavone material is precipitated from the extract by adding water to the extract. In a preferred embodiment, between about 6 to about 8 parts of water are added per part of the concentrated extract. Upon addition of water to the extract some aglucone isoflavone material is precipitated.

To maximize recovery of the aglucone isoflavone material from the extract, the extract and water are thoroughly mixed and then chilled. The extract and water are mixed together for a period of time, preferably between about 30 minutes to about 1 hour. In a preferred embodiment, the extract and water are mixed at a temperature between about 50° C. and about 75° C., most preferably about 70° C. After the water and extract are thoroughly mixed, the mixture is chilled to precipitate the aglucone isoflavone material. Preferably, the extract/water mixture is chilled to between about 5° C. and about 20° C., and most preferably to about 10° C., for a period of time sufficient to precipiatate substantially all of the aglucone isoflavone material. The precipitated aglucone isoflavone material may then be separated from the extract/water mixture in a conventional manner such as by centrifugation or filtration.

The separated aglucone isoflavone material may then be washed with water. In a preferred embodiment, the aglucone isoflavone material is washed with water at a temperature of about 70° C. for about 5 minutes, where the weight ratio of the water wash to the material is between about 0.8:1 and about 2:1. The aglucone isoflavone material is separated from the wash by conventional means such as filtration or centrifugation, and dried. The recovered aglucone isoflavone material typically contains at least 20% genistein and at least 10% daidzein, with the remaining content of the material being formed of residual vegetable materials, including other aglucone isoflavones. The residual vegetable materials are soy materials if the aglucone isoflavone material is isolated from soy whey.

The recovered aglucone isoflavone material may be further purified to produce a high genistein content material containing at least 40% genistein, and preferably at least 90% genistein, and a high daidzein content material containing at least 40% daidzein. The aglucone isoflavone material may be solvated in an aqueous alcohol solvent. Low molecular weight alcohols are preferred as the alcohol component of the solvent, where ethanol is most preferred for food and drug applications because of its low toxicity. The alcohol content of the solvent is preferably between about 30% and about 90%, where an alcohol content of about 80% is most preferred to provide good solvation of the aglucone isoflavone material.

The aqueous alcohol solution containing the solvated aglucone isoflavone material may be contacted with an adsorbent material for a time sufficient to separate the high genistein and high daidzein content materials from the aqueous alcohol solution. In a preferred embodiment, the high genistein and high daidzein content materials are separated from the aqueous alcohol solution by reverse phase HPLC. An HPLC column is prepared as described above, the aqueous alcohol solution containing the aglucone isoflavone material is loaded onto the column, and a high genistein content material and a high daidzein content material are eluted from the column in the manner described above. The high genistein content material contains at least 40% genistein, preferably at least 90% genistein, along with residual vegetable material, which is residual soy material if the genistein is recovered from a soy whey. The high daidzein content material contains at least 40% daidzein, along with residual vegetable material.

Experimental

The present invention is illustrated in more detail by the following examples using a soy whey as the vegetable protein whey. The examples are intended to be illustrative, and should not be interpreted as limiting or otherwise restricting the scope of the invention in any way.

As noted above, soy whey includes the genistein, daidzein, and glycitein "families" of isoflavones having corresponding glucoside, conjugate, and aglucone members, where the genistein family contains the conjugates 6"-OMal genistin and 6"-OAc genistin, the glucoside genistin, and the aglucone genistein; the daidzein family contains the conjugates 6"-OMal daidzin and 6"-OAc daidzin, the glucoside daidzin, and the aglucone daidzein; and the glycitein family contains the conjugate 6"-OMal glycitin, the glucoside glycitin, and the aglucone glycitein. In the following tables the relative concentrations of the isoflavones are measured as a percentage of a family of isoflavones. For example, in the genistein family: % genistin+% 6"-OMal genistin+% 6"-OAc genistin+% genistein=100%. The extent of conversion of conjugates to glucosides, and glucosides to aglucones can be determined by comparing the percentages of each type of compound in an isoflavone family.

EXAMPLE 1

In a first experiment, the conversion of isoflavone conjugates to isoflavone glucosides is examined. The extent of conversion is determined by the quantitative decrease of the percentage of malonate and actate esters of an isoflavone family coupled with a corresponding quantitative increase of the percentage of the glucoside of the same isoflavone family.

The effect of different pH conditions on the first step conversion of isoflavone conjugates to isoflavone glucosides is measured at two different temperatures. Spray dried soy whey is slurried in water to form a 2% solids by weight soy whey suspension. The soy whey is split into two groups of four samples. The samples of each group are adjusted to a pH of 6.0, 7.0, 9.0, and 11.0, respectively. The groups of samples are incubated for 24 hours with one group of samples being incubated at 45° C. and the other group of samples being incubated at 72.5° C. Periodic analysis is conducted on each sample at 0, 2, 4, 6, 8 and 24 hours to determine the isoflavone content of the samples. Table 1 below shows the change and distribution of the isoflavones over the course of the experiment.

TABLE 1

| Sample | GENISTIN | 6"-OMAL GENISTIN | 6"-OAC GENISTIN | GENISTEIN | DAIDZIN | 6"-OMAL DAIDZIN | 6"-OAC DAIDZIN | DAIDZEIN | GLYCITIN | 6"-OMAL GLYCITIN | GLYCITEIN |
|---|---|---|---|---|---|---|---|---|---|---|---|
| pH 6, 45° C. | | | | | | | | | | | |
| t = 0 | 16 | 65 | 0 | 19 | 15 | 65 | 2 | 18 | 32 | 33 | 36 |
| t = 2 hrs | 15 | 62 | 0 | 23 | 15 | 61 | 2 | 21 | 34 | 37 | 28 |
| t = 4 hrs | 13 | 61 | 0 | 26 | 13 | 60 | 2 | 25 | 30 | 34 | 36 |
| t = 6 hrs | 11 | 61 | 0 | 28 | 11 | 60 | 2 | 27 | 30 | 33 | 37 |
| t = 8 hrs | 11 | 60 | 0 | 29 | 10 | 60 | 2 | 28 | 31 | 33 | 36 |
| t = 24 hrs | 24 | 49 | 2 | 25 | 16 | 52 | 0 | 32 | 30 | 27 | 43 |
| pH 7, 45° C. | | | | | | | | | | | |
| t = 0 | 16 | 65 | 0 | 19 | 15 | 65 | 2 | 18 | 32 | 35 | 30 |
| t = 2 hrs | 22 | 59 | 0 | 19 | 20 | 50 | 2 | 19 | 42 | 25 | 34 |
| t = 4 hrs | 22 | 57 | 0 | 21 | 21 | 57 | 1 | 20 | 35 | 32 | 33 |
| t = 6 hrs | 21 | 57 | 0 | 20 | 20 | 58 | 0 | 21 | 40 | 30 | 30 |
| t = 8 hrs | 22 | 56 | 0 | 21 | 21 | 57 | 0 | 22 | 37 | 31 | 33 |
| t = 24 hrs | 17 | 49 | 0 | 15 | 15 | 49 | 0 | 36 | 26 | 28 | 46 |
| H 9, 45° C. | | | | | | | | | | | |
| t = 0 | 16 | 65 | 0 | 19 | 15 | 65 | 2 | 18 | 32 | 32 | 30 |
| t = 2 hrs | 50 | 34 | 0 | 16 | 50 | 34 | 0 | 15 | 50 | 20 | 30 |
| t = 4 hrs | 57 | 27 | 0 | 15 | 57 | 27 | 0 | 16 | 49 | 17 | 34 |
| t = 6 hrs | 62 | 23 | 0 | 15 | 62 | 23 | 0 | 15 | 54 | 13 | 34 |
| t = 8 hrs | 67 | 19 | 0 | 14 | 67 | 18 | 0 | 15 | 57 | 10 | 34 |
| t = 24 hrs | 70 | 17 | 0 | 13 | 63 | 17 | 0 | 20 | 50 | 10 | 39 |
| pH 11, 45° C. | | | | | | | | | | | |
| t = 0 | 16 | 65 | 0 | 19 | 15 | 65 | 2 | 18 | 32 | 33 | 36 |
| t = 2 hrs | 85 | 0 | 0 | 15 | 82 | 0 | 0 | 18 | 62 | 0 | 38 |
| t = 4 hrs | 85 | 0 | 0 | 15 | 81 | 0 | 0 | 19 | 63 | 0 | 37 |
| t = 6 hrs | 86 | 0 | 0 | 14 | 79 | 0 | 0 | 21 | 61 | 0 | 39 |
| t = 8 hrs | 87 | 0 | 0 | 13 | 77 | 0 | 0 | 23 | 60 | 0 | 40 |
| t = 24 hrs | 90 | 0 | 0 | 10 | 53 | 0 | 0 | 47 | 46 | 0 | 54 |
| pH 6, 72.5° C. | | | | | | | | | | | |
| t = 0 | 16 | 65 | 0 | 19 | 15 | 65 | 2 | 18 | 32 | 33 | 36 |
| t = 2 hrs | 33 | 48 | 0 | 19 | 33 | 48 | 2 | 17 | 39 | 27 | 34 |
| t = 4 hrs | 43 | 39 | 0 | 17 | 42 | 39 | 2 | 17 | 46 | 21 | 33 |
| t = 6 hrs | 51 | 33 | 0 | 17 | 49 | 32 | 3 | 17 | 50 | 19 | 31 |
| t = 8 hrs | 56 | 28 | 0 | 16 | 54 | 27 | 3 | 16 | 57 | 14 | 29 |
| t = 24 hrs | 80 | 5 | 0 | 15 | 77 | 5 | 3 | 16 | 66 | 0 | 34 |
| pH 7, 72.5° C. | | | | | | | | | | | |
| t = 0 | 16 | 65 | 0 | 19 | 15 | 65 | 2 | 18 | 32 | 33 | 36 |
| t = 2 hrs | 41 | 43 | 0 | 17 | 41 | 39 | 2 | 17 | 47 | 25 | 29 |
| t = 4 hrs | 52 | 32 | 0 | 15 | 50 | 32 | 2 | 16 | 49 | 18 | 33 |
| t = 6 hrs | 58 | 27 | 0 | 15 | 56 | 26 | 2 | 16 | 51 | 15 | 35 |
| t = 8 hrs | 64 | 21 | 0 | 15 | 62 | 20 | 2 | 16 | 55 | 12 | 32 |
| t = 24 hrs | 59 | 4 | 0 | 38 | 61 | 3 | 0 | 36 | 50 | 0 | 50 |
| pH 9, 72.5° C. | | | | | | | | | | | |
| t = 0 | 16 | 65 | 0 | 19 | 15 | 65 | 2 | 18 | 32 | 33 | 36 |
| t = 2 hrs | 83 | 4 | 0 | 13 | 82 | 4 | 0 | 14 | 64 | 0 | 36 |
| t = 4 hrs | 88 | 2 | 0 | 11 | 84 | 2 | 0 | 15 | 65 | 0 | 35 |
| t = 6 hrs | 90 | 0 | 0 | 10 | 85 | 0 | 0 | 15 | 65 | 0 | 35 |
| t = 8 hrs | 91 | 0 | 0 | 9 | 85 | 0 | 0 | 15 | 65 | 0 | 35 |
| t = 24 hrs | 100 | 0 | 0 | 0 | 85 | 0 | 0 | 15 | 100 | 0 | 0 |
| pH 11, 72.5° C. | | | | | | | | | | | |
| t = 0 | 16 | 65 | 0 | 19 | 15 | 65 | 2 | 18 | 32 | 33 | 36 |
| t = 2 hrs | 86 | 0 | 0 | 14 | 76 | 0 | 0 | 24 | 57 | 0 | 43 |
| t = 4 hrs | 87 | 0 | 0 | 13 | 72 | 0 | 0 | 28 | 54 | 0 | 46 |
| t = 6 hrs | 87 | 0 | 0 | 13 | 67 | 0 | 0 | 33 | 51 | 0 | 49 |
| t = 8 hrs | 88 | 0 | 0 | 12 | 61 | 0 | 0 | 39 | 48 | 0 | 52 |
| t = 24 hrs | 78 | 0 | 0 | 22 | 24 | 0 | 0 | 76 | 31 | 0 | 69 |

As indicated by the relative concentration decreases of the 6"-OMal and the 6"-OAc isoflavone conjugate compounds and the corresponding concentration increases of the glucosides genistin, daidzin, and glycitin, the first conversion step is most rapid and complete at higher, more basic pH conditions and higher temperatures. Substantially complete conversion of the isoflavone conjugates to isoflavone glucosides occurs in the pH 9 and 11 samples at both 45° C. and 72.5° C. The conversion also proceeds to near completion in the pH 6 and 7 samples at 72.5° C.

EXAMPLE 2

In a second experiment, the conversion of isoflavone glucosides to aglucone isoflavones is examined. Isoflavone glucoside enriched whey produced by the first conversion step is used to examine the second conversion step. The extent of conversion is determined by the quantitative decrease of the percentage of the glucoside of an isoflavone family coupled with a corresponding quantitative increase of the percentage of the aglucone of the same isoflavone family.

Soy whey is converted to isoflavone glucoside enriched whey by adjusting the pH of the whey to 11.0 and incubating for 30 minutes at 35° C. One sample of the glucoside enriched whey is incubated at 45° C. for 24 hours to measure conversion of isoflavone glucosides to aglucone isoflavones by residual enzymes in the whey. Other samples of the glucoside enriched whey are inoculated with the following commerically available supplemental enzymes: Biopectinase 100L, Biopectinase 300L, Biopectinase OK70L, Lactase F, Alpha-Gal 600L, G-Zyme G990, Quest Biolactase 30,000, Novo Lactozyme 3000L, Maxilact L2000, Enzeco Fungal Lactase, Pfizer Neutral Lactase, and Quest Neutral Lactase. Samples inoculated with Alpha-Gal 600L, G-Zyme G990, Biopectinase 100L, Biopectinase 300L, Biopectinase OK70L, Lactase F and Enzeco Fungal Lactase are pH adjusted to pH 4.5 prior to inoculation. Samples inoculated with Novo Lactozyme 3000L, Maxilact L2000, Pfizer Neutral Lactase, Quest Biolactase 30,000, and Quest Neutral Lactase are pH adjusted to a pH of 4.5 and 7.0 prior to inoculation. The supplemental enzyme samples are then incubated at 50° C., except the Lactase F sample which is incubated at 35° C., and the Biopectinase 300L and Biopectinase OK70L samples which are incubated at 40° C. Sub-samples are taken after intervals of time and measured for isoflavone content. Table 2 below shows the distribution of isoflavones over the course of the experiment.

TABLE 2

| Sample | GENISTIN | 6"-OMAL GENISTIN | 6"-OAC GENISTIN | GENISTEIN | DAIDZIN | 6"-OMAL DAIDZIN | 6"-OAC DAIDZIN | DAIDZEIN | GLYCITIN | 6"-OMAL GLYCITIN | GLYCITEIN |
|---|---|---|---|---|---|---|---|---|---|---|---|
| Residual enzyme, pH 9.0, 45° C. | | | | | | | | | | | |
| t = 0 | 86 | 5 | 0 | 9 | 79 | 4 | 0 | 18 | 100 | 0 | 0 |
| t = 2 hrs | 89 | 2 | 0 | 9 | 81 | 1 | 0 | 18 | 100 | 0 | 0 |
| t = 4 hrs | 92 | 1 | 0 | 8 | 82 | 0 | 0 | 18 | 100 | 0 | 0 |
| t = 6 hrs | 93 | 0 | 0 | 7 | 82 | 0 | 0 | 18 | 100 | 0 | 0 |
| t = 24 hrs | 0 | 0 | 0 | 100 | 0 | 0 | 0 | 100 | 0 | 0 | 100 |
| Biopectinase 300L, pH 4.5, 40° C. 0.1 g/100 g glucoside enriched whey | | | | | | | | | | | |
| t = 0 | 74 | 0 | 11 | 15 | 100 | 0 | 0 | 0 | 77 | 0 | 23 |
| t = 0.5 hr | 46 | 0 | 0 | 54 | 46 | 3 | 0 | 51 | 75 | 0 | 25 |
| t = 1 hr | 22 | 0 | 0 | 78 | 24 | 3 | 0 | 73 | 66 | 10 | 24 |
| t = 1.5 hrs | 11 | 0 | 0 | 89 | 14 | 3 | 0 | 82 | 73 | 0 | 27 |
| t = 2 hrs | 6 | 0 | 0 | 94 | 7 | 3 | 0 | 90 | 70 | 0 | 30 |
| Biopectinase OK70L, pH 4.5, 40° C. 0.1 g/100 g glucoside enriched whey | | | | | | | | | | | |
| t = 0 | 74 | 0 | 11 | 15 | 100 | 0 | 0 | 0 | 77 | 0 | 23 |
| t = 0.5 hr | 69 | 0 | 0 | 31 | 70 | 0 | 0 | 30 | 76 | 0 | 24 |
| t = 1 hr | 54 | 0 | 0 | 46 | 53 | 3 | 0 | 44 | 76 | 10 | 24 |
| t = 1.5 hrs | 44 | 0 | 0 | 56 | 43 | 0 | 4 | 52 | 75 | 0 | 25 |
| t = 2 hrs | 37 | 0 | 0 | 63 | 35 | 3 | 0 | 62 | 74 | 0 | 26 |
| Biopectinase 100l, pH 4.5, 50° C. 0.04 g/100 g glucoside enriched whey | | | | | | | | | | | |
| t = 0 | 50 | 2 | 0 | 47 | 61 | 2 | 0 | 37 | 60 | 0 | 40 |
| t = 1 hr | 25 | 2 | 0 | 73 | 31 | 2 | 0 | 67 | 54 | 0 | 55 |
| t = 2 hrs | 12 | 2 | 0 | 86 | 15 | 1 | 0 | 83 | 51 | 0 | 50 |
| t = 3 hrs | 7 | 2 | 0 | 92 | 9 | 1 | 0 | 90 | 0 | 0 | 100 |
| Lactase F, pH 4.5, 35° C. 0.1 g/100 g glucoside enriched whey | | | | | | | | | | | |
| t = 0 | 47 | 8 | 0 | 45 | 45 | 7 | 0 | 48 | 74 | 0 | 26 |
| t = 0.5 hr | 9 | 9 | 0 | 82 | 8 | 9 | 0 | 83 | 55 | 0 | 39 |
| t = 1 hr | 3 | 8 | 0 | 89 | 2 | 8 | 0 | 90 | 46 | 0 | 54 |
| t = 2 hrs | 0 | 9 | 0 | 91 | 0 | 8 | 0 | 92 | 32 | 0 | 68 |
| Alpha-Gal 600L pH 4.5, 50° C. 0.1 g/100 g glucoside enriched whey | | | | | | | | | | | |
| t = 0 | 83 | 0 | 0 | 17 | 83 | 0 | 0 | 17 | 80 | 0 | 20 |
| t = 1 hr | 4 | 0 | 0 | 96 | 2 | 0 | 0 | 98 | 23 | 0 | 77 |
| t = 2 hrs | 1 | 0 | 0 | 99 | 0 | 0 | 0 | 100 | 10 | 14 | 76 |
| t = 3 hrs | 0 | 0 | 0 | 100 | 0 | 0 | 0 | 100 | 8 | 14 | 78 |
| Enzeco Fungal Lactase, pH 4.5, 35° C. 0.1 g/100 g glucoside enriched whey | | | | | | | | | | | |
| t = 0 | 83 | 1 | 0 | 16 | 79 | 3 | 1 | 17 | 85 | 0 | 15 |
| t = 0.5 hr | 17 | 1 | 0 | 82 | 16 | 4 | 3 | 77 | 39 | 0 | 55 |
| t = 1 hr | 6 | 1 | 0 | 93 | 5 | 4 | 3 | 87 | 26 | 0 | 74 |
| t = 2 hrs | 0 | 1 | 0 | 99 | 0 | 4 | 3 | 92 | 4 | 0 | 96 |

TABLE 2-continued

| Sample | GENI-STIN | 6"-OMAL GENISTIN | 6"-OAC GENISTIN | GENI-STEIN | DAIDZIN | 6"-OMAL DAIDZIN | 6"-OAC DAIDZIN | DAIDZEIN | GLY-CITIN | 6"-OMAL GLYCITIN | GLY-CITEIN |
|---|---|---|---|---|---|---|---|---|---|---|---|
| G-Zyme G990, pH 4.5, 50° C. 0.1 g/100 g glucoside enriched whey | | | | | | | | | | | |
| t = 0 | 83 | 0 | 0 | 17 | 83 | 0 | 0 | 17 | 80 | 0 | 20 |
| t = 1 hr | 49 | 1 | 0 | 51 | 41 | 0 | 0 | 59 | 82 | 0 | 18 |
| t = 2 hrs | 30 | 1 | 0 | 69 | 21 | 0 | 0 | 79 | 79 | 0 | 21 |
| t = 3 hrs | 18 | 0 | 0 | 82 | 11 | 0 | 0 | 89 | 69 | 11 | 19 |
| Novo Lactozyme 3000L, 50° C. 0.2 g/100 g glucoside enriched whey pH 4.5 | | | | | | | | | | | |
| t = 0 | 78 | 7 | 0 | 15 | 77 | 7 | 0 | 16 | 75 | 6 | 19 |
| t = 1 hr | 78 | 8 | 0 | 14 | 80 | 7 | 0 | 13 | 86 | 0 | 14 |
| t = 4 hrs | 77 | 8 | 0 | 15 | 80 | 7 | 0 | 13 | 84 | 0 | 16 |
| pH 7.0 | | | | | | | | | | | |
| t = 0 | 78 | 7 | 0 | 15 | 77 | 7 | 0 | 16 | 75 | 6 | 19 |
| t = 1 hr | 72 | 8 | 0 | 20 | 77 | 7 | 0 | 16 | 72 | 0 | 28 |
| t = 4 hrs | 68 | 8 | 0 | 24 | 74 | 7 | 0 | 19 | 61 | 0 | 39 |
| Maxilact L2000, 50° C. 0.2 g/100 g glucoside enriched whey pH 4.5 | | | | | | | | | | | |
| t = 0 | 78 | 7 | 0 | 15 | 77 | 7 | 0 | 16 | 75 | 6 | 19 |
| t = 1 hr | 78 | 7 | 0 | 15 | 77 | 7 | 0 | 16 | 75 | 6 | 19 |
| t = 4 hrs | 76 | 7 | 0 | 17 | 76 | 7 | 0 | 17 | 73 | 6 | 21 |
| pH 7.0 | | | | | | | | | | | |
| t = 0 | 78 | 7 | 0 | 15 | 77 | 7 | 0 | 16 | 75 | 6 | 19 |
| t = 1 hr | 71 | 7 | 0 | 22 | 73 | 6 | 0 | 21 | 56 | 7 | 31 |
| t = 4 hrs | 65 | 7 | 0 | 28 | 69 | 5 | 0 | 26 | 52 | 0 | 48 |
| Pfizer Neutral Lactase, 50° C. 0.2 g/100 g glucoside enriched whey pH 4.5 | | | | | | | | | | | |
| t = 0 | 78 | 7 | 0 | 15 | 77 | 7 | 0 | 16 | 75 | 6 | 19 |
| t = 1 hr | 77 | 7 | 0 | 16 | 77 | 6 | 0 | 17 | 73 | 7 | 20 |
| t = 4 hrs | 77 | 0 | 7 | 16 | 77 | 6 | 0 | 17 | 76 | 0 | 24 |
| pH 7.0 | | | | | | | | | | | |
| t = 0 | 78 | 7 | 0 | 15 | 77 | 7 | 0 | 16 | 75 | 6 | 19 |
| t = 1 hr | 70 | 7 | 0 | 23 | 72 | 5 | 0 | 23 | 70 | 6 | 24 |
| t = 4 hrs | 55 | 7 | 0 | 38 | 60 | 6 | 0 | 34 | 66 | 0 | 34 |
| Quest Biolactase 30,000, 50° C. 0.2 g/100 g glucoside enriched whey pH 4.5 | | | | | | | | | | | |
| t = 0 | 78 | 7 | 0 | 15 | 77 | 7 | 0 | 16 | 75 | 6 | 19 |
| t = 1 hr | 0 | 6 | 0 | 94 | 0 | 6 | 0 | 94 | 0 | 0 | 100 |
| t = 4 hrs | 0 | 4 | 0 | 96 | 0 | 5 | 0 | 95 | 0 | 0 | 100 |
| pH 7.0 | | | | | | | | | | | |
| t = 0 | 78 | 7 | 0 | 15 | 77 | 7 | 0 | 16 | 75 | 6 | 19 |
| t = 1 hr | 2 | 7 | 0 | 91 | 3 | 7 | 0 | 90 | 29 | 0 | 71 |
| t = 4 hrs | 0 | 7 | 0 | 93 | 0 | 6 | 0 | 94 | 0 | 0 | 100 |
| Quest Neutral Lactase, 50° C. 0.2 g/100 g glucoside enriched whey pH 4.5 | | | | | | | | | | | |
| t = 0 | 78 | 7 | 0 | 15 | 77 | 7 | 0 | 16 | 75 | 6 | 19 |
| t = 1 hr | 73 | 6 | 0 | 21 | 76 | 5 | 0 | 19 | 79 | 0 | 21 |
| t = 4 hrs | 73 | 6 | 0 | 21 | 76 | 5 | 0 | 19 | 76 | 0 | 24 |
| pH 7.0 | | | | | | | | | | | |
| t = 0 | 78 | 7 | 0 | 15 | 77 | 7 | 0 | 16 | 75 | 6 | 19 |
| t = 1 hr | 2 | 7 | 0 | 91 | 7 | 4 | 0 | 89 | 15 | 0 | 15 |
| t = 4 hrs | 0 | 7 | 0 | 93 | 0 | 4 | 0 | 96 | 0 | 0 | 100 |

As shown by the conversion of genistin, daidzin, and glycitin to genistein, daidzein, and glycitein, respectively, substantially complete conversion of the isoflavone glucosides to aglucone isoflavones is acheived. The supplemental enzymes remarkably increase the rate of the conversion, effecting substantially complete conversion within 1 hour with certain supplemental enzymes. The supplemental enzymes found most effective at pH 4.5 are Biopectinase 100L, Biopectinase 300L, Lactase F, Alpha-Gal 600L, G-Zyme G990, Quest Biolactase 30,000, and Enzeco Fungal Lactase. Supplemental enzymes found most effective at pH 7.0 are Quest Biolactase 30,000 and Quest Neutral Lactase.

EXAMPLE 3

In another experiment, an aglucone isoflavone whey protein material is recovered from 5 an aglucone isoflavone enriched soy whey. A first sample of aglucone isoflavone enriched soy whey weighing 1000 g containing 30 mg of genistein, 37 mg of daidzein, and 7 mg of glycitein is concentrated by evaporation over low heat to 163 g (concentration ratio—1:6.1). The concentrated whey is heated to coagulate protein material in the whey, and is centrifuged to further concentrate the whey protein material. 21 g of whey protein material containing 25 mg of genistein, 32 mg of daidzein, and 6 mg of glycitein is separated from the whey. The recovered whey protein material contains 82% of the genistein, 88% of the daidzein, and 77% of the glycitein in the combined whey and whey protein material.

A second sample of aglucone isoflavone enriched soy whey weighing 400g and containing 12 mg of genistein, 15 mg of daidzein, and 3 mg of glycitein is heated to coagulate protein material in the whey without concentrating the whey. The coagulated whey protein material and the whey are centrifuged to further concentrate the whey protein material. 8.7 g of whey protein material is recovered containing 5 mg of genistein, 7 mg of daidzein, and 1 mg of glycitein. The recovered whey protein material contains 44% of the genistein, 47% of the daidzein, and 34% of the glycitein in the combined whey protein material and the whey.

Comparing the whey protein materials of the first and second samples, it is clear that concentrating the aglucone isoflavone enriched whey before separating the whey protein material results in increased capture of the aglucone isoflavones in the whey protein material.

EXAMPLE 4

In another experiment, an aglucone isoflavone material is recovered by extracting an aglucone isoflavone whey protein material with an aqueous alcohol extract and precipitating the aglucone isoflavone material from the extract.

Eight hundred twenty one grams of aglucone isoflavone whey protein material containing 86% protein dry basis, 4.7 g genistein, 2.2 g daidzein, and 0.36 g glycitein is provided by converting the isoflavone conjugates and isoflavone glucosides in the whey to aglucone isoflavones and recovering the aglucone isoflavone whey protein material from the whey. The aglucone isoflavone whey protein material is extracted with 6360 g of an 80:20 percent by weight ethanol/water solution (7.7:1 solution/aglucone isoflavone whey protein material) at 60° C. for 45 minutes. After extraction, the resulting slurry is cooled to 25° C. and filtered over Whatman No. 4 filter paper under vacuum. A wet cake weighing 1584 g containing 798 g of solids, 0.8 g of genistein, 0.4 g daidzein, and 0.02 g of glycitein is recovered along with 3397 g of a clear extract containing 23 g of solids, 3.9 g of genistein, 1.8 g of daidzein, and 0.34 g of glycitein.

The cake is extracted a second time with 2000 g of 80:20 percent by weight ethanol/water solution (2.3:1 solution/initial aglucone isoflavone whey protein material) at 25° C. for 5 minutes. After the second extraction, the resulting slurry is again filtered over Whatman No. 4 filter paper. A wet cake weighing 1542 g and containing 794 g of solids, 0.3 g of genistein, 0.1 g of daidzein, and 0.01 g of glycitein is recovered along with a second extract weighing 2042 g and containing 4.0 g of solids, 0.5 g genistein, 0.3g daidzein, and 0.01 glycitein. The extracts are combined, and contain 94% of the genistein and 95% of the daidzein initially in the aglucone isoflavone whey protein material.

The extracts are then concentrated by evaporating in a Buchi evaporator under vacuum at 70° C. to 1528 g (20% of the original combined extract volume). 6000 g of deionized water is added to the concentrated extract (4:1 water/extract). White isoflavone precipitates form when the water is added. The precipitate slurry is heated to 70° C. for 45 minutes. The slurry is then refrigerated at 4° C. for 24 hours to allow the isoflavone precipitates to form and settle. 7300 g of supertanant is decanted away from the precipitate, and the remaining slurry is centrifuged to recover the precipitate. The recovered precipitate is washed again with 600 g of deionized water at 70° C. for 15 minutes. The precipitate is recovered by centrifugation and dried under vacuum at 50° C.

A dried aglucone isoflavone material weighing 7.3 g and containing 49% genistein, 19% daidzein, and 4% glycitein is obtained.

EXAMPLE 5

In another experiment, a high genistein content material and a high daidzein content material are separated from an aglucone isoflavone material by reverse phase HPLC. Two grams of aglucone isoflavone material containing 55% genistein, 21% daidzein, and 4% glycitein, dry basis, is added to 1 liter of 50:50 percent by weight methanol/water solution. The solution is filtered through a Whatman No. 5 filter paper, and then through a 0.45 $\mu$ filter.

The solution is then loaded onto a 2" diameter by 25 cm long HPLC column packed with Kromsil packing material (Kromasil C18 16 $\mu$m, 100 Å beads). A mobile phase consisting of 50:50 percent by weight methanol/water solution is then passed through the column at a rate of 64 ml/minute. The appearance of the daidzein, glycitein, and genistein from the column effluent is detected by UV adsorption. Daidzein is collected in a first fraction and genistein is collected in a second fraction. The daidzein and genistein fractions are evaporated to remove the alcohol, causing the high genistein and high daidzein content materials in each respective fraction to precipitate. The preciptitated high genistein and high daidzein content materials are recovered by centrifugation and dried in a vacuum oven. The recovered high genistein content material contains about 95% genistein, and the recovered high daidzein content material contains about 45% daidzein.

In the above described experiments, all percentages indicated for 6"-OMal-genistin, 6"-OAc-genistin, 6"-OMal-daidzin, 6"-OAc-daidzin, 6"-OMal-glycitin, and glycitein are calculated values. The percentages indicated of enzyme concentration are calculated from grams of commercial enzyme preparation per 100 grams whey solids or per 100 g whey in each sample.

The following is a description of a method for quantifying isoflavones in soy products. The isoflavones are extracted from soy products by mixing 0.75 gram of sample (spray dried or finely ground powder) with 50 ml of 80/20 methanol/water solvent. The mixture is shaken for 2 hours at room temperature with an orbital shaker. After 2 hours, the remaining undissolved materials are removed by filtration through Whatman No. 42 filter paper. Five ml of the filtrate are diluted with 4 ml of water and 1 ml of methanol.

The extracted isoflavones are separated by HPLC (High Performance Liquid Chromatography) using a Hewlett Packard C18 Hypersil reverse phase column. The isoflavones are injected onto the column and eluted with a solvent gradient starting with 88% methanol, 10% water, and 2% glacial acetic acid. At a flow rate of 0.4 ml/min., all the isoflavones—genistin, 6"-O-Acetylgenistin, 6"-O-Malonylgenistin, genistein, daidzin, 6"-O-Acetyldaidzin, 6"-O-Malonyldaidzin, daidzein, glycitin, 6"-O-Malonylglycitin, and glycitein—are clearly resolved. Peak detection is by UV absorbance at 260 nm. Identification of the peaks was performed by HPLC-mass spectrometer.

Quantification is achieved by using pure standards (genistin, genistein, daidzin, and daidzein) purchased from Indofine Chemical Company, Sommerville, N.J. Response factors (integrated area/concentration) are calculated for each of the above compounds and are used to quantitate unknown samples. For the conjugated forms for which no pure standards are available, response factors are assumed to be that of the parent molecule but corrected for molecular weight difference. The response factor for glycitin is assumed to be that for genistin corrected for molecular weight difference.

This method provides the quantities of each individual isoflavone. For convenience, total genistein, total daidzein, and total glycitein can be calculated, and represent the aggregate weight of these compounds if all the conjugated forms are converted to their respective unconjugated forms. These totals can also be measured directly by a method using acid hydrolysis to convert the unconjugated forms.

The foregoing are merely preferred embodiments of the invention. Various changes and alterations can be made without departing from the spirit and broader aspects thereof as set forth in the appended claims, which are to be interpreted in accordance with the principles of patent law including the Doctrine of Equivalents.

What is claimed is:

1. A process for producing an aglucone isoflavone enriched vegetable protein whey from a vegetable protein whey containing isoflavone conjugates, comprising:
    a.) treating said vegetable protein whey at a temperature and pH for a time period sufficient to convert at least a majority of isoflavone conjugates to isoflavone glucosides; and
    b.) contacting an enzyme with said isoflavone glucosides in said vegetable protein whey at a temperature and a pH for a time period sufficient to convert at least a majority of the isoflavone glucosides to aglucone isoflavones.

2. The process as set forth in claim 1 wherein the vegetable protein whey is treated at a pH value of about 6 to about 13.7 and at a temperature between about 2° C. and about 121° C. to convert the isoflavone conjugates to isoflavone glucosides.

3. The process as set forth in claim 2 wherein the vegetable protein whey is treated at a pH value between about 9 and about 10 and at a temperature between about 45° C. and about 73° C.

4. The process as set forth in claim 3 wherein the time period to convert the isoflavone conjugates to isoflavone glucosides is between about 4 hours and about 6 hours.

5. The process as set forth in claim 2 wherein the vegetable protein whey is treated at a pH value between about 10 and about 11 and at a temperature between about 5° C. and about 50° C.

6. The process as set forth in claim 5 wherein the time period to convert the isoflavone conjugates to isoflavone glucosides is between about 0.5 hour and about 1 hour.

7. The process as set forth in claim 1 wherein at least 80% of said isoflavone conjugates are converted to isoflavone glucosides.

8. The process as set forth in claim 7 wherein at least 90% of said isoflavone conjugates are converted to isoflavone glucosides.

9. The process as set forth in claim 1 wherein said enzyme is contacted with the isoflavone glucosides in the vegetable protein whey at a temperature between about 5° C. and about 75° C. and a pH value between about 3 and about 9.

10. The process as set forth in claim 9 wherein said enzyme is contacted with the isoflavone glucosides in the vegetable protein whey at a temperature between about 35° C. and about 45° C.

11. The process as set forth in claim 9 wherein contacting an enzyme with said isoflavone glucosides in said vegetable protein whey comprises adding an effective amount of a supplemental enzyme to the vegetable protein whey.

12. The process as set forth in claim 11 wherein the supplemental enzyme comprises a saccharidase enzyme capable of cleaving 1,4-glucoside bonds.

13. The process as set forth in claim 12 wherein the supplemental enzyme is selected from a group comprising alpha-glucosidase enzymes, beta-glucosidase enzymes, beta-galactosidase enzymes, gluco-amylase enzymes, pectinase enzymes, and combinations thereof.

14. The process as set forth in claim 1 wherein at least 80% of said isoflavone glucosides are converted to aglucone isoflavones.

15. The process as set forth in claim 14 wherein at least 90% of said isoflavone glucosides are converted to aglucone isoflavones.

16. The process as set forth in claim 1 wherein said vegetable protein whey comprises soybean whey.

17. The process as set forth in claim 1 further comprising recovering an aglucone isoflavone whey protein material containing protein and aglucone isoflavones from said aglucone isoflavone enriched vegetable protein whey.

18. The process as set forth in claim 17 wherein said aglucone isoflavone whey protein material is recovered by at least one of ultrafiltration, heat coagulation, and dewatering.

19. The process as set forth in claim 17 wherein said aglucone isoflavone whey protein material is recovered by chilling said vegetable protein whey and separating said aglucone isoflavone whey protein material from said chilled whey.

20. The process as set forth in claim 17 wherein said aglucone isoflavone whey protein material is recovered from concentrated vegetable protein whey.

21. The process as set forth in claim 17 further comprising:
    a.) extracting said aglucone isoflavone whey protein material with an extractant effective to extract aglucone isoflavones from said aglucone isoflavone whey protein material to produce an aglucone isoflavone enriched extract; and
    b.) contacting said extract with an adsorbent material for a time sufficient to separate a high genistein content material from said extract.

22. The process as set forth in claim 21 wherein said extractant includes between about 30% alcohol to about 90% alcohol.

23. The process as set forth in claim 21 wherein said extractant has a pH value of about the isoelectric point of said protein in said aglucone isoflavone whey protein material.

24. The process as set forth in claim 23 wherein said extractant has a pH value of between about 3 and about 6.

25. The process as set forth in claim 21 wherein said aglucone isoflavone whey protein material is extracted with said extractant where a weight ratio of extractant to whey protein material does not exceed about 11:1.

26. The process as set forth in claim 21 wherein said aglucone isoflavone whey protein material is extracted with two portions of said aqueous alcohol extractant where a combined weight ratio of said portions of said extractant to said whey protein material does not exceed a total weight ratio of about 11:1.

27. The process as set forth in claim 21 wherein said adsorbent material is particulate.

28. The process as set forth in claim 21 wherein contacting said extract with an adsorbent material further comprises releasably binding genistein in said extract with said adsorbent material.

29. The process as set forth in claim 21 wherein said extract is eluted through said adsorbent material with an eluent to separate a high genistein content material from said extract.

30. The process as set forth in claim 21 wherein said high genistein content material contains at least 40% genistein.

31. The process as set forth in claim 30 wherein said high genistein content material contains at least 90% genistein.

32. The process as set forth in claim 17 further comprising:
 a.) extracting said aglucone isoflavone whey protein material with an extractant effective to extract aglucone isoflavones from said aglucone isoflavone whey protein material to produce an aglucone isoflavone enriched extract; and
 b.) contacting said extract with an adsorbent material for a time sufficient to separate a high daidzein content material from said extract.

33. The process as set forth in claim 32 wherein said extractant is an aqueous alcohol containing between about 30% alcohol to about 90% alcohol.

34. The process as set forth in claim 32 wherein said extractant has a pH value of about the isoelectric point of said protein in said aglucone isoflavone whey protein material.

35. The process as set forth in claim 34 wherein said extractant has a pH value of between about 3 and about 6.

36. The process as set forth in claim 32 wherein said aglucone isoflavone whey protein material is extracted with said extractant where a weight ratio of extractant to whey protein material does not exceed about 11:1.

37. The process as set forth in claim 32 wherein said aglucone isoflavone whey protein material is extracted with two portions of said aqueous alcohol extractant where a combined weight ratio of said portions of said extractant to said whey protein material does not exceed a total weight ratio of about 11:1.

38. The process as set forth in claim 32 wherein said adsorbent material is particulate.

39. The process as set forth in claim 32 wherein contacting said extract with an adsorbent material further comprises releasably binding daidzein in said extract with said adsorbent material.

40. The process as set forth in claim 32 wherein said extract is eluted through said adsorbent material with an eluent to separate a high daidzein content material from said extract.

41. The process as set forth in claim 32 wherein said high daidzein content material contains at least 40% daidzein.

42. The process as set forth in claim 17 further comprising:
 a.) extracting said aglucone isoflavone whey protein material with an aqueous alcohol extractant to produce an aglucone isoflavone enriched extract; and
 b.) contacting said extract with an adsorbent material for a time sufficient to separate a glycitein containing material from said extract.

43. The process as set forth in claim 17 further comprising:
 a.) extracting said aglucone isoflavone whey protein-- material with an aqueous alcohol extractant to produce an aglucone isoflavone enriched extract;
 b.) concentrating said aglucone isoflavone enriched extract to between about 15% and about 30% of its original volume; and
 c.) precipitating an aglucone isoflavone material by adding water to said extract.

44. The process as set forth in claim 43 wherein said aqueous alcohol extractant contains between about 30% and about 90% alcohol.

45. The process as set forth in claim 43 wherein said aglucone isoflavone whey protein material is extracted with said extractant where a weight ratio of extractant to whey protein material does not exceed about 11:1.

46. The process as set forth in claim 43 wherein said aglucone isoflavone whey protein material is extracted with two portions of said aqueous alcohol extractant where a combined weight ratio of said portions of said extractant to said whey protein material does not exceed a total weight ratio of 11:1.

47. The process as set forth in claim 43 wherein said aqueous alcohol extractant has a pH value of about the isoelectric point of said protein in said aglucone isoflavone whey protein material.

48. The process as set forth in claim 47 wherein said aqueous alcohol extractant has a pH value of between about 3 and about 6.

49. The process as set forth in claim 43 wherein water is added to said extract where a weight ratio of water to extract is between about 6:1 and about 8:1.

50. The process as set forth in claim 43 further comprising washing the precipitated aglucone isoflavone material with water, where a weight ratio of water to said aglucone isoflavone material is between about 0.8:1 and about 2:1.

51. The process as set forth in claim 43 further comprising chilling the extract and water to maximize precipitation of said aglucone isoflavone material.

52. The process as set forth in claim 43 further comprising:
 a.) solvating said aglucone isoflavone material in an aqueous alcohol solution; and
 b.) contacting said aqueous alcohol solution containing said solvated aglucone isoflavone material with an adsorbent material for a time sufficient to separate a high genistein content material from said aqueous alcohol solution.

53. The process as set forth in claim 44 further comprising:
 a.) solvating said aglucone isoflavone material in an aqueous alcohol solution; and
 b.) contacting said aqueous alcohol solution containing said solvated aglucone isoflavone material with an adsorbent material for a time sufficient to separate a high daidzein content material from said aqueous alcohol solution.

* * * * *